US006884320B2

United States Patent
Karlsson et al.

(10) Patent No.: US 6,884,320 B2
(45) Date of Patent: Apr. 26, 2005

(54) METHOD AND APPARATUS FOR PRODUCING AND TESTING A FIBER BED

(75) Inventors: Hakan Karlsson, Åkersberga (SE); Per-Ivar Fransson, Åkersberga (SE)

(73) Assignee: Fibertracker AB, Akersberga (SE)

( * ) Notice: Subject to any disclaimer, the term of this patent is extended or adjusted under 35 U.S.C. 154(b) by 299 days.

(21) Appl. No.: 10/103,734

(22) Filed: Mar. 25, 2002

(65) Prior Publication Data

US 2002/0134522 A1 Sep. 26, 2002

(30) Foreign Application Priority Data

Mar. 23, 2001 (EP) .............................. 01850053

(51) Int. Cl.[7] .............................. D21F 1/06; D21F 1/08; D21C 7/06
(52) U.S. Cl. ......................... 162/49; 162/198; 162/258; 162/259; 162/263; 73/53.03; 73/53.04; 73/159
(58) Field of Search .......................... 162/49, 198, 259, 162/263; 73/37.7, 53.03, 53.04, 159

(56) References Cited

U.S. PATENT DOCUMENTS 3,186,215 A * 6/1965 Danforth .................. 73/53.04
3,355,250 A 11/1967 Gorring
3,538,749 A 11/1970 Danforth
4,344,321 A 8/1982 Haapamaki

FOREIGN PATENT DOCUMENTS

WO    WO 95/34804    12/1995

* cited by examiner

Primary Examiner—Steve Alvo
(74) Attorney, Agent, or Firm—Young & Thompson

(57) ABSTRACT

A method for producing and testing a fiber bed, includes a housing, a main inlet passage and a main outlet passage, a cavity in the housing in fluid connection with the inlet and outlet passages, a body rotatably arranged in the cavity, the body being arranged with a through-going passage having first and a second opening, a screen arranged in the through-going passage, and elements for measuring properties of the fiber bed. The method includes positioning the body so that the first opening is connected to the main inlet and the second opening is connected to the main outlet, creating a first passage, leading a fiber suspension through the first passage in order to produce a fiber bed on the screen, measuring the properties of the bed, rotating the body such that the second opening is connected to the main inlet and the first opening is connected to the main outlet and creating a flow through the first passage for removing the fiber bed from the screen through the outlet.

11 Claims, 5 Drawing Sheets

METHOD AND APPARATUS FOR PRODUCING AND TESTING A FIBER BED

TECHNICAL AREA

The present invention relates to a method for producing and testing a fiber bed, including a housing, a main inlet passage and a main outlet passage, a cavity in said housing in fluid connection with said inlet and outlet passages, a body rotatably arranged in said cavity, said body being arranged with a through-going passage having a first and a second opening, a screen arranged in said through-going passage, and means for measuring properties of the fiber bed. The present invention also relates to a device for performing the method.

TECHNICAL BACKGROUND

In the area of paper making there is a frequent need for measuring the fiber suspension in order to evaluate different properties of the fibres, the suspension and the fiber web both during forming and after dying.

One important factor is how well the fiber web dewaters during forming. Improving the efficiency of the paper web forming is a major object in all papermaking. In order to be able to determine the performance of a furnish on the paper machine it is necessary to know how fast water drains from that particular furnish and how much water can be expected to be removed by mechanical means such as vacuum.

One such method is described in U.S. Pat. No. 4,613,406 where a suspension sample of a certain volume is led through a screen. A vacuum pump is arranged on the collection container situated after the screen. A pressure recorder on the collection container monitors the pressure value. During build-up of a fiber bed the pressure difference across the fiber bed is measured as a function of time and provides a graph with distinct inflections, which inflections indicate different stages of dewatering of the fiber bed.

The apparatus according to U.S. Pat. No. 4,613,406 is basically a laboratory instrument rather than a device to be used in a more frequent control of an operating paper machine. In that respect an apparatus according to U.S. Pat. No. 4,969,351 has been developed. The apparatus comprises a container for suspension and a sheet mold mechanism comprising a movable table under the container, where the table includes a number of sheet forming locations. Underneath the container and the table is a dropleg. With the apparatus series of samples may be tested in the above mentioned fashion to determine the dewatering aspects of the samples, where it is possible to perform sequential tests with different sheet weight and to obtain data regarding drainage time versus basis weight.

The apparatus exhibits a rather complex constructional design in that the container and the dropleg are arranged movable to and from the table in order to allow the table to be moved so that a sheet forming location may be aligned with the container and the dropleg. This means that there must be sufficient sealing between the parts in order for the suspension not to leak out. As is very common with pulp suspensions, the fibers tend to get stuck and to build up in various places, which may deteriorate the sealing function, and possibly also the total function of the apparatus.

Further, with the apparatuses described above, the produced fiber bed must be removed mechanically afterwards.

Other measurements include moisture measurements on a fiber bed. In those cases an infrared light source, transmitting two narrow bands of infrared radiation, and a detector are utilised in order to establish the transmittances through the paper. The ratio of these transmittances is a function of the water weight per unit area. U.S. Pat. No. 4,823,008 discloses such an apparatus used in the production line of a paper making machine. However, the measuring of the moisture content is not performed in connection with the measuring of dewatering properties, and includes a device movable transversal to the feeding direction of the web with the source on one side of the web and the detector on the other side of the web.

Other values that can be measured on the fiber bed or the web is the test of the kappa number, which refers to the amount of material remaining in the pulp, where the material is often equated with the lignin content of the fibers. One way of detecting the lignin content is to illuminate the fibers with ultraviolet UV-light and to measure the fluorescence of the lignin, thereby obtaining the kappa number. One such device is disclosed in U.S. Pat. No. 5,486,915.

The devices according to the state of the art are rather bulky and complicated in order to fulfil requirements like compact, easy to use and to clean from previous paper beds and that is capable of performing several different tests if required.

BRIEF DESCRIPTION OF THE INVENTION

The object of the present invention is to provide a device for producing a fiber bed in a simple and time-efficient way without the drawbacks of the devices according to the state of the art as regards both forming and removal of the fiber bed, and that can perform measurements and tests on the fiber bed.

This object is solved according to the invention by a method characterised by claim 1 and by a device characterised according to claim 2. Further preferred embodiments of the invention are characterised by the dependent claims.

According to one aspect of the invention the method is characterised in positioning said body so that the first opening is connected to the main inlet and the second opening is connected to the main outlet, creating a first passage, leading a fiber suspension through the first passage in order to produce a fiber bed on the screen, measuring the properties of the bed, rotating said body such that the second opening is connected to the main inlet and the first opening is connected to the main outlet and creating a flow through the first passage for removing said fiber bed from the screen through the outlet.

The device is characterised in that said body is capable of being positioned so that the first opening is connected to the main inlet and the second opening is connected to the main outlet, creating a first passage, allowing for a fiber suspension to be led through the first passage in order to produce a fiber bed on the screen and to measure the properties of the bed, and that said body is capable of being rotated such that the second opening is connected to the main inlet and the first opening is connected to the main outlet and means for creating a flow through the first passage for removing said fiber bed from the screen through the outlet.

According to another aspect it is characterised in that the measuring means comprises pressure measurement means for measuring the pressure difference over the fiber bed.

According to yet another aspect it is characterised in that the housing is arranged with a second passage, and that the body is capable of being rotated such that the through-going passage of the body is in communication with the second passage, and in that means for measuring properties of the produced fiber bed are arranged in the second passage.

According to a further aspect it characterised in that the means for measuring properties comprises light radiation and detection means for measuring the moisture content of the fiber bed and for the lignin content of the fiber bed.

Preferably the housing is arranged with a third passage, that, when the through-going passage of the body is also in communication with the second passage, it is also in communication with the third passage and forms a passage through the device. Preferably drying means is arranged in the passage to dry the produced fiber bed.

The advantages of the present invention is that a very compact and yet versatile device is obtained for producing and testing of a fiber bed. When measuring dewatering of a fiber bed a conventional build-up of fibers on a screen is performed by flowing the suspension through the device. When the measurements have been performed, it is an easy task to remove the fiber bed by just turning the body and flush the device, thereby removing the fiber bed.

With other measurements such as moisture content and lignin content, the body is turned so that the passage through the device is shut off, and is placed so that the fiber bed is accessible via an opening in the device for different light sources and sensors. Further, it is possible to dry the fiber bed in the device by connecting the passage in the body to a drying means, which produces an air flow through the fiber bed. The device comprises very few movable parts, and the body acts as a valve for closing off the inlet when measurements are to be performed other than dewatering measurements. This also means that special measurements, like optical measurements, may be performed without having to remove the fiber bed from the screen.

The device allows the testing of several important aspects on a fiber bed in a very simple and fast way, thus providing a device, which may be used continuously in a paper making process.

These and other aspects of, and advantages with, the present invention will become apparent from the following detailed description of a preferred embodiment and from the accompanying drawings.

BRIEF DESCRIPTION OF THE DRAWINGS

In the following detailed description of the invention, reference will be made to the accompanying drawings, of which

DETAILED DESCRIPTION OF THE INVENTION

Figure 1:
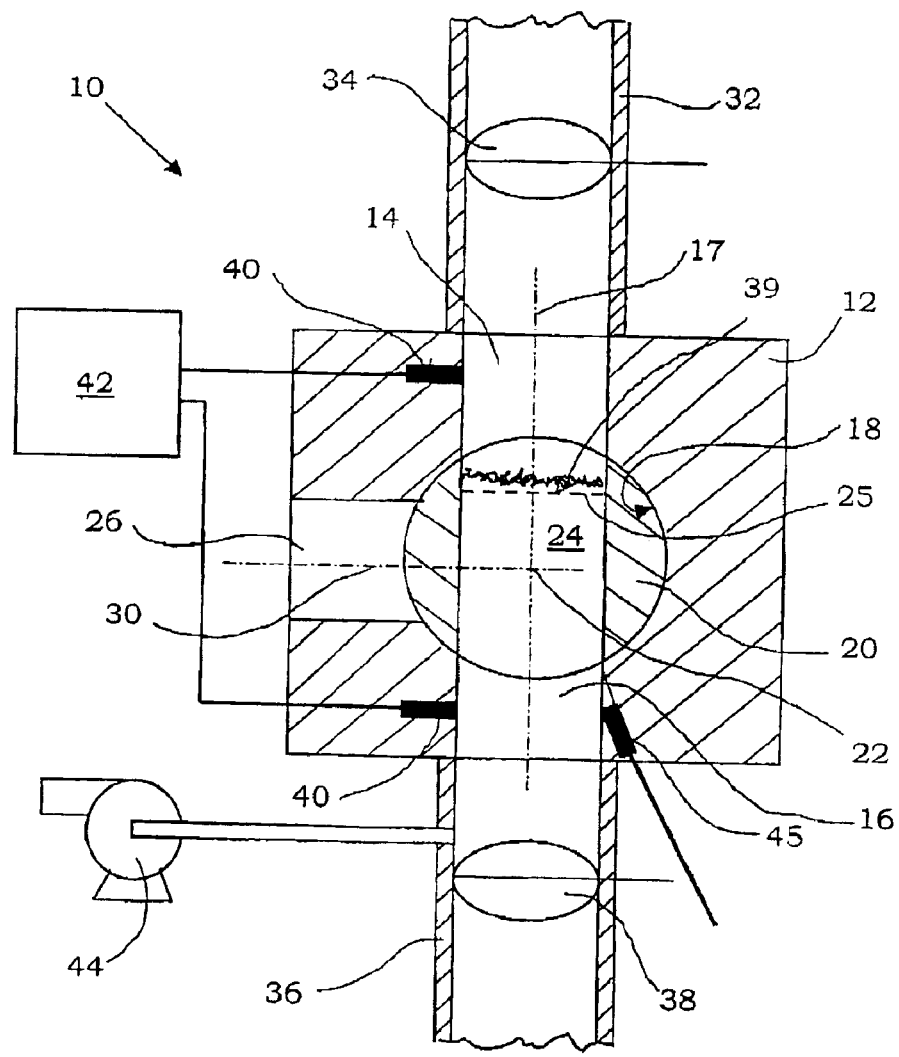
FIG. 1 is a schematic cross-sectional view of a device according to the invention in first position.

The present invention relates to the testing of pulp quality and comprises a device indicated in the schematic drawings with reference numeral 10. It comprises a housing 12 with a main inlet 14 and a main outlet 16 arranged opposite the inlet so that the inlet and outlet are in line with each other along a first centre line 17. The housing is arranged with a cavity 18, which in the embodiment shown in drawings 1–3 is essentially with a spherical form. A body 20 is arranged in the cavity, which body has the corresponding spherical form, and which is rotatable around an axis of rotation 22 by means of a rotating means (not shown) such as for example a handle, an electric motor or a cylinder/piston arrangement.

The body is arranged with a through-going passage 24, which passage has substantially the same cross-sectional area and form as the main inlet and outlet. In one position of the body, the openings of the through-going passage are in communication with the main inlet and main outlet respectively, forming a first passage through the device. Inside the through-going passage, a screen 25 is in this case arranged substantially transversal to the extension of the passage. The design of the embodiment shown has certain similarities to conventional ball valves, which design as such is not novel but provides certain advantages for the present invention, which will become apparent from the following.

The housing is further provided with at least one second passage 26 with a centre Line 30, arranged in the embodiment shown 90° to the first centre line, the function of which second passage will be described in detail below. The second passage is in communication with the cavity 18 and the outside of the housing. The centre line 30 of the second passage 26, centre line of the main inlet and outlet 17 and the axis of rotation of the body 22 intersect at the centre of the body.

The main inlet 14 is connected via conduits 32 to a fiber suspension source (not shown), which may be a suspension line or an intermediate container, depending on the type of production line, type of application and/or type and frequency of the measurements The conduit may further be provided with valve means 34 for controlling the flow to the device according to the invention.

The main outlet 16 is connected via conduits 36 to a drain for the reject. Depending on the type of measurement, the reject may be collected for further measuring or testing or be led back to the production line or to the sewage. The conduit may be provided with valve means 38 for controlling the outflow from the device according to the invention.

When a suspension is to be tested, the body is in the position of FIG. 1. When testing drainage time of the fiber suspension a sample with a specified volume per time unit is fed through the first passage of the device whereby the pulp forms a bed 39 on the screen. The pressure differential as a function of time is recorded by suitable means, for example a set of pressure transducers 40 arranged upstream and downstream the screen, electrically connected to a recorder 42 capable of recording pressure differential as a function of time, preferably the time to reach a certain pressure difference.

In this context it is naturally conceivable to connect a vacuum pump 44 to the conduit of the main outlet, for example a constant volume pump. According to known techniques the recorded measurements from the pressure transducers 40 provide values on how difficult the pulp is to dewater, i e the drainage quality of the pulp suspension.

Another way to test the drainage time is to have a constant pressure and to measure the water volume passing the screen as a function of time. In this context it is to be understood that a number of different methods of measuring the dewatering properties are applicable to the present invention.

Figure 2:
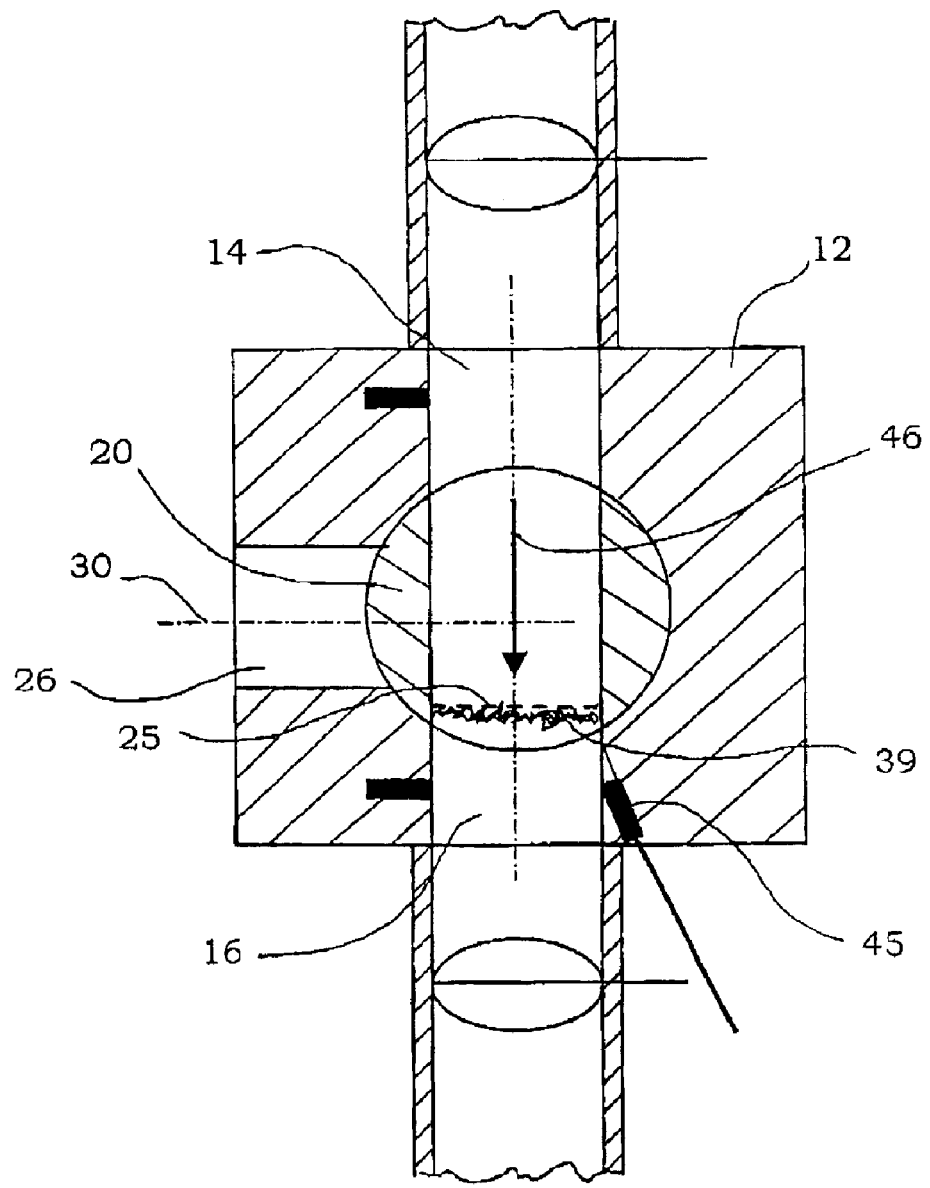
FIG. 2 is a view corresponding to FIG. 1 in a second position.

When the test is performed, the body 20 is rotated 180° around its axis 22 so that the screen 25 is positioned adjacent the main outlet 16, FIG. 2. The device may preferably be arranged with water nozzles 45 arranged downstream the screen and directed towards the screen. In the embodiment shown the nozzles are arranged in the outlet passage. The nozzles 45 are connected to a water pressure source (not shown) via conduits. During rotation of the body, the nozzles spray against the screen and the fiber bed for aiding in removing the fiber bed by lifting it from the screen. The rotation of the body and the direction of the nozzle means that the spray jet covers almost the entire surface of the fiber bed, and from different angles, thereby enhancing the removing effect. When the body has rotated 180°, the fiber bed 39 is placed on the outlet side. A cleaning flow 46 is provided through the device, which flow removes the fiber bed from the screen by the pressure. The body 20 may now be rotated back to its initial position for further measurements.

Figure 3:
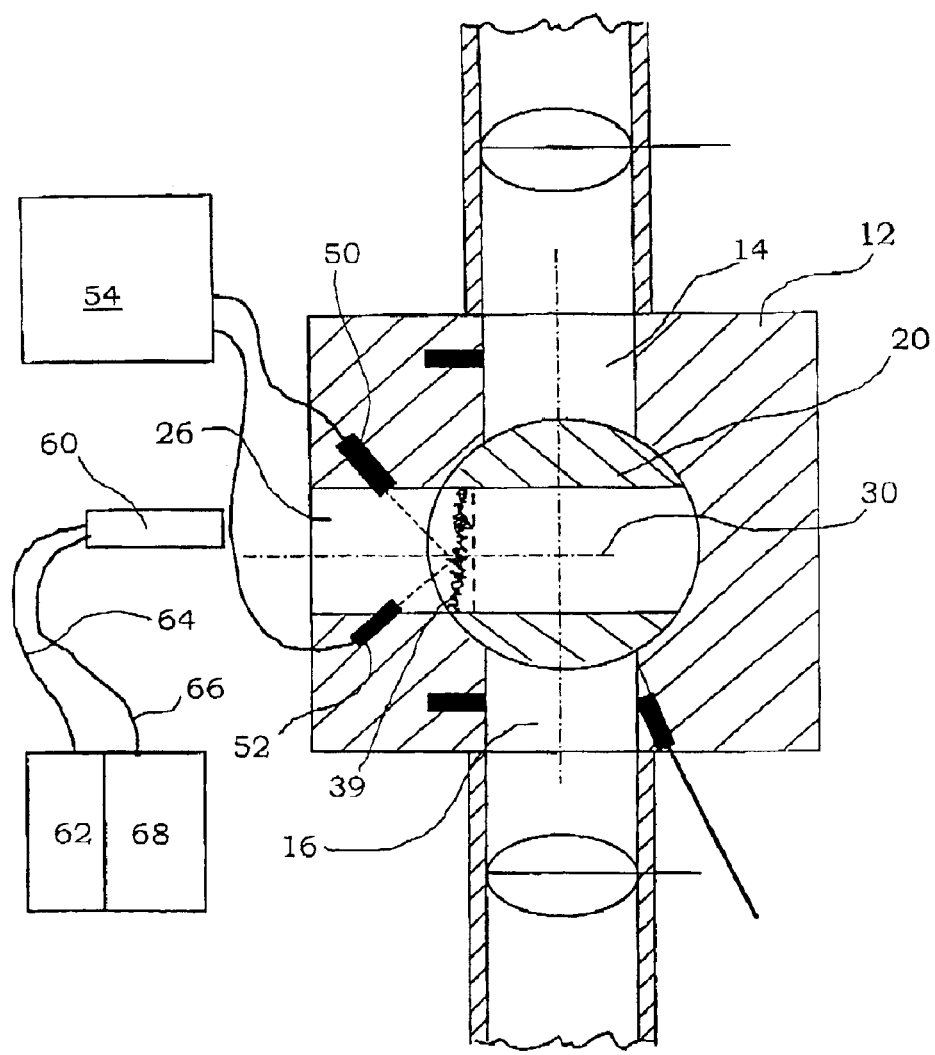
FIG. 3 is a view corresponding to FIG. 1 in a third position.

If further or other measurements are to be performed than dewatering, the device utilises the second passage 26. After the build-up of a fiber bed as described above, with or without the pressure measurements, the body is rotated 90°, FIG. 3. Thereby the first passage between the main inlet and the main outlet is closed by the body. The through-going passage of the body and the screen with its fiber bed is now accessible via the second passage 26.

Here further tests may be conducted on the fiber bed. It is possible to measure the moisture content of the fiber bed with the help of an infrared light source 50 and a detector 52 connected to a control unit 54, capable of controlling the light source, obtaining the signals from the detector and processing the signals. The light source transmits two or several narrow bands of infrared radiation, and the detector detects the reflected light for each band in order to establish the properties of the paper. One property is the water weight per unit area, i e how hard the moisture is tied to the fibers, which is calculated in the control unit.

Further, the device according to the invention may be used for measuring the lignin content of the fiber bed. Then a probe assembly 60 may be arranged adjacent the second passage. The probe assembly may comprise fiber optics where a light source 62 transmits UV light via a set of fibers 64 to the probe, which illuminates the fiber bed 39. The resultant fluorescent light is collected by the probe optics and is led via a second set of fibers 66 to an analyser/detector 68.

It is also possible to arrange a near-IR assembly 54 adjacent the second passage for measuring the chemical composition of the fiber bed comprising a near-IR light source, light detectors and filters. When illuminating the fiber bed with near-IR light the reflected spectrum is collected by the detectors and fed to an analysing means for evaluation of the chemical composition.

Figure 4:
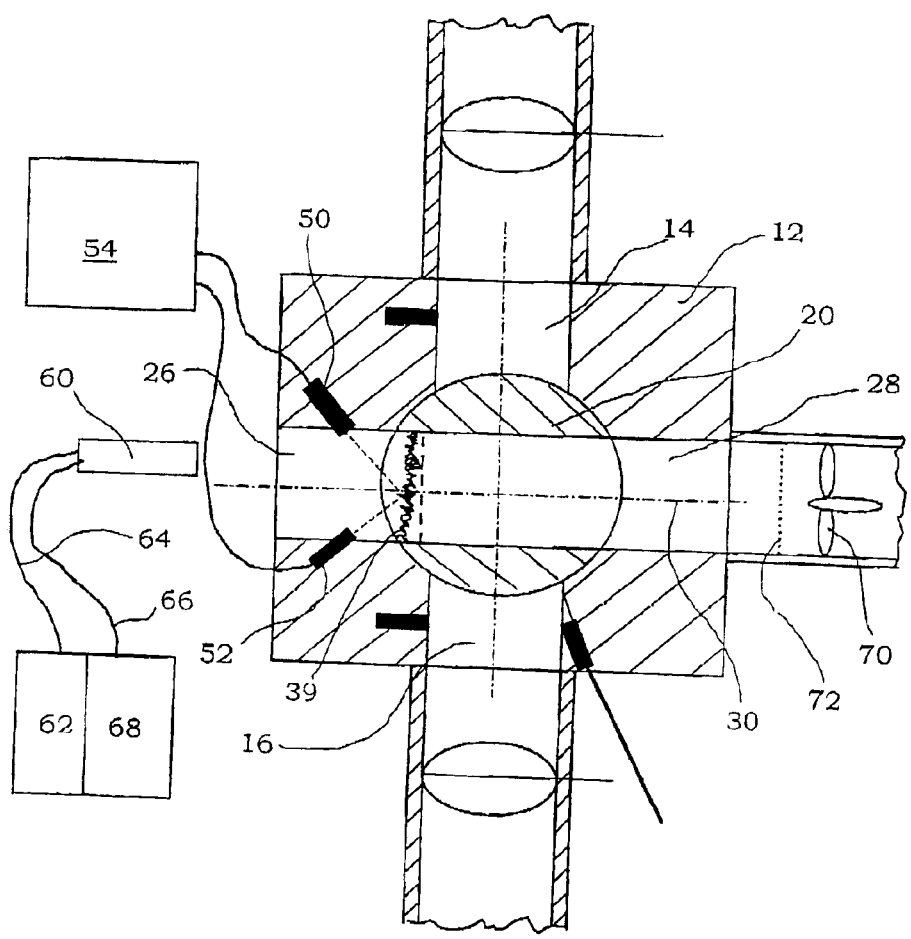
FIG. 4 shows an alternative embodiment of the invention.

In that context, the device may be provided with a third passage, FIG. 4, situated on the opposite side of the second passage whereby the second and third passages and the passage of the body are in line with each other along a second centre line 30 and form a through-going passage. A drying means such as a fan or the like 70, and a heating coil 72 is arranged in or adjacent the third passage, which blows hot air through the passage and through the fiber bed, It is also conceivable to remove the dried fiber bed with for example pressurised air and to weigh the bed on a scale.

Figure 5:
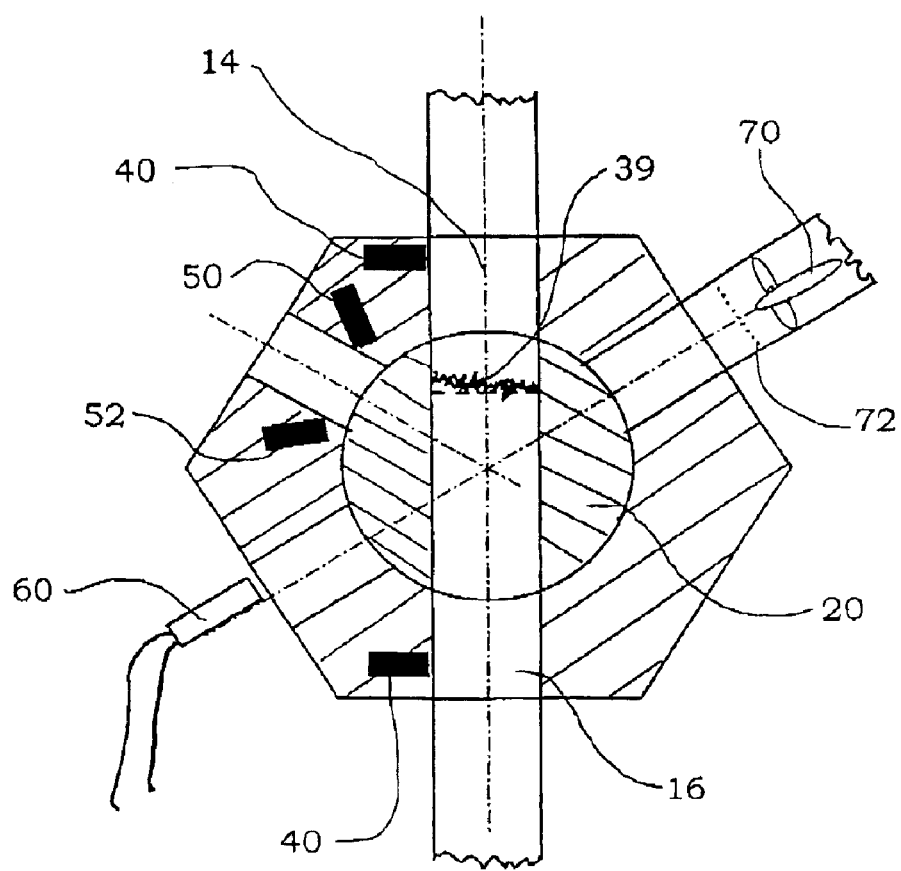
FIG. 5 shows an further embodiment of a device according to the present invention.

It is to be understood that the device described above and shown in the drawings are to be regarded as non-limiting examples of the present invention and that it is defined by the patent claims. For example the device may have a different design than shown in the embodiment described such as that the cavity may be circle-cylindrical and with the corresponding shape of the body. It is also conceivable to have further passages in order to create more than one measuring station. FIG. 5 shows an example where moisture content is measured at one station and the lignin content is measured at a second station, where also the dried fiber bed may be removed or ejected and then weighted.

A further conceivable development of the present invention is to arrange more devices on top or beside each other where all the main inlets are connected to a common supply conduit and where all the main outlets are connected to a common outlet, Fig. Each device is then operated separate from each other, and each device with its own valve means at the inlet and outlet. By this arrangement, the different devices may perform different stages of the measuring and/or perform different measurements, so that a continuous measuring of the fiber suspension can be performed, and also that sequential measurements with different sheet weight may be performed.

What is claimed is:

1. Method for producing and testing a fiber bed (39), includes a housing (12), a main inlet passage (14) and a main outlet passage (16), a cavity (18) in said housing in fluid connection with said inlet and outlet passages, a body (20) rotatably arranged in said cavity, said body being arranged with a through-going passage (24) having a first and a second opening, a screen (25) arranged in said through-going passage and adjacent to the second opening, and means (40) far measuring properties of the fiber bed, characterised in positioning said body so that the first opening is connected to the main inlet and the second opening is connected to the main outlet, creating a first passage, leading a first suspension through the first passage in order to produce a fiber bed on the screen, measuring the properties of the bed, rotating said body such that the second opening is connected to the main inlet and the first opening is connected to the main outlet and creating a flow through the first passage for removing said fiber bed from the screen through the outlet.

2. Device (10) for producing and testing a fiber bed (39), which includes a housing (12), a main inlet passage (14) and a main outlet passage (16), a cavity (18) in said housing in fluid connection with said inlet and outlet passages, a body (20) rotatably arranged in said cavity, said body being arranged with a through-going passage (24) having a first and a second opening, a screen (25) arranged in said through-going passage and adjacent to the second opening, and means (40) for measuring properties of the fiber bed, characterised in that said body is capable of being positioned so that the first opening is connected to the main inlet and the second opening is connected to the main outlet, creating a first passage, allowing for a fiber suspension to be led through the first passage in order to produce a fiber bed on the screen and to measure the properties of the bed, and that said body is capable of being rotated such that the second opening is connected to the main inlet and the first opening is connected to the main outlet and means for creating a flow through the first passage for removing said fiber bed from the screen through the outlet.

3. Device according to claim 2, characterised in that the measuring means comprises pressure measurement means for measuring the pressure difference over the fiber bed.

4. Device according to claim 2, characterised in that the housing is arranged with a second passage (26), and that the body is capable of being rotated such that the through-going passage of the body is in communication with the second passage, and in that means for measuring properties of the produced fiber bed (50, 52, 60) are arranged in connection to the second passage.

5. Device according to claim 4, characterised in that the means for measuring properties comprises light radiation and detection means for measuring the moisture content of the fiber bed.

6. Device according to claim 4, characterised in that the means for measuring properties comprises UV light radiation and detection means for measuring the lignin content of the fiber bed.

7. Device according to claim 4, characterised in that the means for measuring properties comprises near-IR light radiation and detection means for measuring the chemical composition of the fiber bed.

8. Device according to claim 3, characterised in that the housing is arranged with a third passage (28), and in that, when the through-going passage of the body is in communication with the second passage, it is also in communication with the third passage and forms a passage through the device.

9. Device according to claim 8, characterised in that a drying means (70) is arranged to be able to dry the produced fiber bed.

10. Device according to claim 3, characterised in that the housing is arranged with a second passage (26), and that the body is capable of being rotated such that the through-going passage of the body is in communication with the second passage, and in that means for measuring properties of the produced fiber bed (50, 52, 60) are arranged in connection to the second passage.

11. Device (10) for producing and testing a fiber bed (39), including a housing (12), a main inlet passage (14) and a main outlet passage (16), a cavity (18) in said housing in fluid communication with said inlet and outlet passages, a body (20) rotatably arranged in said cavity, said body being arranged with a through-going passage (24) having a first and a second opening, a screen (25) arranged in said through-going passage and adjacent to the second opening, and means (40) for measuring properties of the fiber bed, characterised by means positioning said body so that the first opening is connected to the main outlet and the second opening is connected to the main outlet, means providing a first passage, means for leading a fiber suspension through the first passage in order to produce a fiber bed on the screen, means for measuring the properties of the bed, means for rotating said body such that the second opening is connected to the main outlet and the first opening is connected to the main outlet, and means creating a flow through the first passage for removing said fiber bed from the screen through the outlet.

* * * * *